| United States Patent [19] | [11] Patent Number: 5,002,893 |
| Rosenthal | [45] Date of Patent: Mar. 26, 1991 |

[54] SINGLE COLOR READING METHOD FOR DETERMINING FRUCTOSAMINE

[75] Inventor: Murray A. Rosenthal, Akron, Ohio

[73] Assignee: Isolab, Inc., Akron, Ohio

[21] Appl. No.: 937,107

[22] Filed: Sep. 19, 1985

[51] Int. Cl.$^5$ ............... G01N 21/78; G01N 33/66; G01N 33/68

[52] U.S. Cl. .................................. 436/87; 435/25; 436/88; 436/95; 436/175; 436/825; 436/904

[58] Field of Search .............. 436/175, 177, 34, 63, 436/67, 87, 88, 95, 111, 164, 903, 904, 178, 825; 435/25

[56] References Cited

U.S. PATENT DOCUMENTS

| 4,166,763 | 9/1979 | Esders et al. | 435/25 X |
| 4,168,205 | 9/1979 | Danninger et al. | 435/10 |
| 4,455,371 | 6/1984 | Richardson et al. | 435/25 |
| 4,554,254 | 11/1985 | Krystal | 436/164 X |
| 4,610,963 | 9/1986 | Matsui et al. | 435/25 X |
| 4,642,295 | 2/1987 | Baker | 436/87 |

OTHER PUBLICATIONS

Johnson et al., Clin. Chim. Acta., vol. 127, pp. 87–95, 1982.

*Primary Examiner*—Robert J. Hill, Jr.
*Attorney, Agent, or Firm*—Oldham & Oldham Co.

[57] ABSTRACT

A single color determination method of quantization of the amount of fructosamine in a sample such as serum by removing other interfering reducing agents and developing a color with a coloring agent such as tetrazolium salt.

8 Claims, No Drawings

SINGLE COLOR READING METHOD FOR DETERMINING FRUCTOSAMINE

TECHNICAL FIELD

This invention relates to a single color reading method for determining fructosamine and thus glucose levels in samples such as blood to aid in detecting diabetes and monitoring diabetes status in patients. More particularly, this invention relates to an end point type method of determining fructosamine levels as distinguished from a kinetic method.

BACKGROUND ART

Colorometric methods of determining fructosamine levels in samples such as blood serum using reagents that produce a color change due to the reducing action of fructosamine are well known as illustrated by John Richard Baker's European Patent No. 0,085,263. The Baker European Patent uses a basic treatment of blood serum with a dye selected from tetrazolium salts, e.g., tetranitro blue, tetrazolium, or preferably nitroblue tetrazolium which, when reduced, changes to a highly colored blue (purple) formazan dye having a broad absorbance peak at about 535 nm. The Baker method uses two color readings with a definite time interval therebetween to develop a kinetic color change which is utilized to calculate from standards the fructosamine level or content. As is well known, kinetic methods are difficult to perform manually with precision, due to the exact timing required.

DISCLOSURE OF INVENTION

This invention utilizes a single color reading method for determining fructosamine that allows greater freedom from the timing sequence required in the kinetic method. Reducing agents present in serum other than the fructosamine, e.g., ascorbate and glutathione are eliminated prior to addition of the tetrazolium salt. A further advantage of this inventio is that, once the interferences, i.e., the other reducing agents, are eliminated, any color formed is due only to the reaction between fructosamine and the tetrazolium salt; therefore, the fructosamine reaction can be stopped, which makes the timing of the color determination les critical. Thus, the addition of a solution that halts the reaction between the fructosamine and the tetrazolium coloring agent allows the spectrophotometric reading to be done on a non-timed basis and thus the color measurements can be performed at the operator's convenience rather than at a particular time as required by the kinetic method. The primary advantage of a single color measurement is that it takes less time than the Baker method.

BEST MODE FOR CARRYING OUT THE INVENTION

In one aspect of this method a sample is taken such as a blood sample, and it is then treated to remove or destroy the reducing agents such as ascorbate and/or glutathione to leaving fructosamine. This treatment to eliminate the other reducing agents or interfering substances may consist of any one of the following methods (hereinafter referred to as the elimination of interfering substances step):

1. Incubation of sample for long periods of time at low temperatures either with or without a base, preferably a strong base.
2. Incubation of sample at high temperatures either with or without a base, preferably strong.
3. Incubation of sample at high pH, at least 10 or higher.
4. Desalting the sample via dialysis or gel permeation chromatography.
5. Adding one or more oxidizing agents which would oxidize interferences but not fructosamine.
6. Adding enzymes which would convert interfering substance(s) to a form (s) that will not react with the coloring reagent.

After the interfering substances have been removed for the sample, it is then mixed with the coloring reagent and incubated for a period of time. The amount of color formed is measured photometrically and is proportional to the amount of fructosamine in the sample. A serum blank may also be run in order to subtract out any background color due to the color of the serum.

Of the phsiologically relevant reducing substances present in blood serum, including glucose, fructose, glucosamine, creatinine, and urate, only ascorbate and glutathione show significant interferences with tetrazolium and related dye reductions. Thus, by eliminating or destroying ascorbate and glutathione in samples, it is possible to then determine fructosamine content with a single color determination.

Interference form reducing substances in the sample, other than fructosamine, can be lowered and/or eliminated by one or more of the methods discussed previously. In the preferred method, serum is mixed with a small volume of base for instance sodium hydroxide solution to raise its pH to about 10. The sample is allowed to sit at room temperature for at least 30 minutes. This effectively eliminates the interference. The treated sample is then assayed for fructosamine content according to the Baker patent methodology, except that only one color reading is taken. It is important for all samples, standards, blanks, etc., to be assayed under identical conditions. The reaction of fructosamine with tetroazolium is very dependent on factors such as pH, time and temperature being the same. These factors must all be controlled in order to assure that the amount of color generated in proportional to the fructosamine concentration in all samples.

EXAMPLES

The following examples are given for the purpose of illustrating the present invention.

Example 1

A serum sample was aliquoted and admixed with the following solutions on a microliter by volume basis at ambient temperature:

| Trial | Serum | 1.1 mM Ascorbate | 0.4 N NaOH | H$_2$O |
| --- | --- | --- | --- | --- |
| A | 500 | 0 | 0 | 100 |
| B | 500 | 50 | 0 | 50 |
| C | 500 | 0 | 50 | 50 |
| D | 500 | 50 | 50 | 0 |

The following tetrazolium color reagent was used:
(0.12 M Na$_2$CO$_3$/NaHCO$_3$ pH 10.8),
11.64 g Na$_2$CO$_3$,
0.52 g NaHCO$_3$,
adjust to pH 10.8 with NaOH,
0.29 g 2-(4-iodophenyl) -3-(4-nitrophenyl)-5-phenyl tetrazolium chloride (INT)
up to 1 litter with deionized water.

Exactly 30 minutes after four serum trials were mixed, 20 microliters of each trial was mixed with 1 mL of color reagent. The color was allowed to develop for 900 seconds (12 minutes) and the absorbance at 500 nm was immediately read for each trial on a suitable spectrophotometer. The resultant absorbances were:

| Trial | Absorbance 500 nm |
|---|---|
| A | .121 |
| B | .148 |
| C | .118 |
| D | .121 |

Trial D which contained ascorbate and was treated with sodium hydroxide solution showed no interference from ascorbate. Trial B which contained ascorbate, but was not treated with sodium hydroxide solution showed interference.

Example 2

A serum sample was aliquoted, admixed on a microliter by volume basis, and incubated as follows:

|  | TRIAL | | | |
|---|---|---|---|---|
|  | A | B | C | D |
| Serum | 500 | 500 | 500 | 500 |
| Ascorbate (1.1 mM) | 0 | 50 | 0 | 50 |
| H$_2$O | 50 | 0 | 50 | 0 |
| Incubation Temp. °C. | 4 | 4 | 37 | 37 |

The samples were allowed to incubate for 200 minutes and were then assayed as in Example 1. The resultant asorbances were:

| Trial | Absorbance 500 nm |
|---|---|
| A | .105 |
| B | .117 |
| C | .100 |
| D | .105 |

These trials demostrate that elevated temperatures can be used to eliminate ascorbate interference. Further, this example demonstrates that temperatures of 37° C. and higher is adequate for removing interfering substances in the sample.

Example 3

A serum sample containing 1.3 mM 1-deoxy, 1-morpholino fructose (DMF) was treated as in Example 1. The resultant absorbances were:

| Trial | Absorbance 500 nm |
|---|---|
| A | .158 |
| B | .181 |
| C | .159 |
| D | .161 |

This shows that DMF, a synthetic fructosamine compound which is used to prepare standards for this test, is not effected by this sample preparation step.

Example 4

A serum sample was treated as in Example 1, except 2.0 mM mecuric acetate an oxidizing agent was substituted for the sodium hydroxide solution. The resultant absorbances were:

| Trial | Absorbance 500 nm |
|---|---|
| A | .141 |
| B | .153 |
| C | .121 |
| D | .126 |

This demostrates the ability of mercuric ion to reduce the interference caused by ascorbate.

Example 5

A serum sample was treated as in Example 1, except reduced glutathione (obtained from Sigma Chemical) at a concentration of 10 mM was substituted for the ascorbic acid solution.

The resultant absorbances were:

| Trial | Absorbance 500 nm |
|---|---|
| A | .090 |
| B | .135 |
| C | .087 |
| D | .084 |

These trials demostrate that glutathione interference can also be removed by a 30 minute incubation with sodium hydroxide.

Example 6

A serum sample was treated as in Example 1, except ascorbate oxidase spatulas (obtained from Boehringer, Mannheim Biochemicals, Indianapolis, Ind., product #736619) were substitued for the sodium hydroxide solution in trials C and D. Also, the following volumes of water on a microliter basis were used to dilute the serum: A and C —50, B and D—0. The spatulas contain about 17 unis of ascorbate oxidase enzyme (E.C. #1.10.3.3) which is used to remove ascorbic acid from aqueous solutions. The spatulas were used to mix the serum occasionally throughout the 30 minute incubation.

The resultant ascorbances were:

| Trial | Absorbance 500 nm |
|---|---|
| A | .076 |
| B | .105 |
| C | .077 |
| D | .081 |

These trials demostrate the ability of ascorbate oxidase to reduce the interference caused by ascorbate.

Example 7

A serum sample was desalted using gel permeation chromatogrophy. The serum sample was split into two 500 microliter portions. Fifty microliters of water was added to the first portion and 50 microliters of 1.1 mM ascorbic acid was added to the second portion. Two desalting columns (obtained from Isolab, Inc., product #QS-2B) were equilibrated with isotonic saline. Five hundred microliters of each portion was added to a separate column and was allowed to elute. Next 300 microliters of isotonic saline was added to each column and was allowed to elute. Receivers were placed beneath the columns and 500 microliters of isotonic saline was added to each column and the eluate collected. This eluate contained the desalted serum.

The desalted eluates were aliquoted and admixed on a microliter basis with the following solutions:

| Trial | Eluate | Amount of Eluate | 1.1 mM Ascorbate | H$_2$O |
|---|---|---|---|---|
| A | Portion 1 | 200 | 0 | 20 |
| B | Portion 1 | 200 | 20 | 0 |
| C | Portion 2 | 200 | 0 | 20 |

Next, 50 microliters of each trial was admixed with 1 mL of the color reagent in Example 1. The color was allowed to develop as in Example 1. The resultant absorbances were:

| Trial | Absorbance 500 nm |
|---|---|
| A | .078 |
| B | .228 |
| C | .074 |

These trials demostrate that desalting the sample prior to the fructosamine assay eliminates ascorbate interference.

Example 8

Three serum samples were treated as in Example 1, Trial B, stored at 4° C., and assayed as in Trial 1 on days 0, 1, and 4. DMF standards were run on each day to calibrate the relationship between absorbance and DMF content analogous to the method in the Baker patent. Also, the sample blanks wre subtracted. The resultant concentrations of fructosamine in the sample are shown in the following table:

TABLE 1

| Day Sample No. | mM fructosamine (as DMF equivalents) | | |
|---|---|---|---|
| | 1 | 2 | 3 |
| 0 | 1.40 | 1.33 | 2.63 |
| 1 | 1.35 | 1.38 | 2.82 |
| 4 | 1.11 | 1.12 | 2.38 |

This demonstrates that ascorbate interference can be reduced, just by storing the sample at 4° C.

Example 9

A continuous flow autoanalyzer was used to perform the fructosamine assay. As in Example 2 of the Baker patent, a Technicon Autoanalyzer (Technicon Instruments Corp., Tarrytown, N.Y.) was used. The analyzer was programmed to allow one part sample to mix with three parts of 15 mM sodium hydroxide solution. This mixture was heated at 37° C. for five minutes. The analyzer was then programmed to mix in three parts (for a total of seven parts) of the tetrazolium color reagent of Example 1 with the above mixture. This mixture was incubated for two minutes at 37°C. The analyzer was programmed to then read the absorbance at 500 nm. One normal and one elevated serum sample were mixed as in Example 1, Trials A and B, and analyzed immediately. The resultant absorbances were:

| Sample | Ascorbate Added | Absorbance 500 nm |
|---|---|---|
| Normal | No | .112 |
| Normal | Yes | .113 |
| Elevated | No | .196 |
| Elevated | Yes | .194 |

Example 10

One normal and one elevated serum sample was treated as in Example 1, Trial D. Exactly 30 minutes after the serum trials were mixed, 20 microliters of each trial was mixed with 1 mL of color reagent. The color was allowed to develop for 900 seconds at which time 2.0 mL of 1 N-hydrochloric acid was added and mixed in order to stop the reaction. The absorbance of each tube was measured at 5, 10, and 30 minutes after the acid was added. The resultant absorbances were:

| Trial | Serum | Absorbance 500 nm | | |
|---|---|---|---|---|
| | | 5 Minutes | 10 Minutes | 30 Minutes |
| A | Normal | .063 | .064 | .063 |
| B | Elevated | .113 | .113 | .111 |

This demonstrates that the reaction can be stopped and that the generated color remains stable. This allows the color measurement to be performed at a convenient time. The reaction between the coloring agent and fructosamine may be stopped by adding an acid to reduce pH to below 5.

These examples have demonstrated that the interfering substances are eliminated by treating the sample with a strong base, an oxidizing agent, or by desalting.

The pH level of the sample is controlled to between 10 and 14 and usually 10.5 and 10.8 by adding strong bases such as sodium hydroxide or buffers like sodium carbonate or sodium bicarbonate.

While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A method of determining the level of fructosamine in a blood sample or a sample derived from blood, said method comprising the steps of eliminating any interfering substances from the sample, controlling the pH of the sample to a value between 10 and 14, adding a coloring agent to the sample and, after a delay, taking a color measurement and determining the fructosamine level in said sample by comparing a single color measurement with that of a single color measurement on a standard solution, wherein the coloring agent and pH conditions are selected such that a change of color in the coloring agent is caused by glucose in the sample that has reacted or associated with an amine group of protein and has undergone a molecular rearrangement to form fructosamine.

2. The method as in claim 1 wherein interfering substances are eliminated by treating the sample with a strong base.

3. The method as in claim 1 wherein the pH of the sample is controlled to a value between 10.5 and 10.8.

4. The method as in claim 1 wherein the pH of the sample is controlled by adding a buffer to the sample, said buffer comprising sodium carbonate and sodium bicarbonate in suitable proportions.

5. The method of claim 1 wherein the coloring agent is tetrazolium salt.

6. The method of claim 1 wherein the salt is 2-(4-iodophenyl)-3-(4-nitrophenyl)-5-phenyl tetrazolium choride.

7. A mehod of determining the fructosamine level in a sample, said method comprising the steps of eliminating any interfering substances from the sample and controlling the pH of the sample to a value between 10 and 14, adding a coloring agent to the sample capable of reacting with fructosamine to develop a color and, after a delay, taking a single color measurement and determining the fructosamine level in said sample by comparing single color measurement with a color developed with said coloring agent and standard fructosamine solution, wherein any reaction between the coloring agent and fructosamine in the sample is stopped by an acid.

8. The method of claim 7 wherein the pH is lowered to below 5.

* * * * *